United States Patent
Lee et al.

(10) Patent No.: US 7,886,571 B2
(45) Date of Patent: Feb. 15, 2011

(54) APPARATUS FOR MEASURING ADHESIVE AND FRICTIONAL PROPERTIES OF POLYMER

(75) Inventors: Hak-joo Lee, Daejeon (KR); Shin Hur, Daejeon (KR); Jae-hyun Kim, Daejeon (KR); Seung-woo Han, Daejeon (KR); Jung-yup Kim, Daejeon (KR); Ki-ho Cho, Daejeon (KR)

(73) Assignee: Korea Institute of Machinery & Materials (KR)

( * ) Notice: Subject to any disclaimer, the term of this patent is extended or adjusted under 35 U.S.C. 154(b) by 1672 days.

(21) Appl. No.: 11/132,508

(22) Filed: May 19, 2005

(65) Prior Publication Data

US 2006/0171579 A1 Aug. 3, 2006

(30) Foreign Application Priority Data

Jan. 31, 2005 (KR) .................. 10-2005-0008818

(51) Int. Cl.
*G06K 9/00* (2006.01)
*G01D 18/00* (2006.01)

(52) U.S. Cl. ..................... 73/1.01; 382/199
(58) Field of Classification Search .............. 73/9, 73/10, 54.04, 379.06, 529, 54.22, 150 R, 73/864.71; 382/199, 200, 206, 286
See application file for complete search history.

(56) References Cited

U.S. PATENT DOCUMENTS

| | | | | |
|---|---|---|---|---|
| 3,902,371 A | * | 9/1975 | Hooper et al. | ........... 73/864.24 |
| 4,400,978 A | * | 8/1983 | Guay et al. | .................. 73/453 |
| 4,856,342 A | * | 8/1989 | Bottenbruch et al. | .......... 73/827 |
| 2003/0190872 A1 | * | 10/2003 | Arai et al. | ..................... 451/42 |

OTHER PUBLICATIONS

Bhushan, "Thin film friction and adhesion studies using atomic force microscopy," Feb. 2000, Journal of Applied Physics, vol. 87, No. 3.*
Dimension 3000 Atomic Force Microscope User Manual printed by University of Minnesota.*

* cited by examiner

*Primary Examiner*—Vu Le
*Assistant Examiner*—Alex Liew
(74) *Attorney, Agent, or Firm*—Cantor Colburn LLP

(57) ABSTRACT

Disclosed herein is an apparatus for measuring adhesive and frictional properties of a polymer hemisphere relative to a contact plate provided in the apparatus. The apparatus comprise a body having a movable table installed to move along an X-axis and Y-axis and a vertical column positioned at a rear side of the movable table, a sample mount provided on the movable table and having a mirror to reflect surface images of a horizontal contact plate, a head assembly located at a front side of the column and having a polymer hemisphere used to press a surface of the contact plate to implement an adhesive force test, a camera device located at a front side of the mirror to capture the surface images of the contact plate during the adhesive force test, and a control device for analyzing various data inputted thereto during the adhesive force test.

19 Claims, 4 Drawing Sheets

APPARATUS FOR MEASURING ADHESIVE AND FRICTIONAL PROPERTIES OF POLYMER

BACKGROUND OF THE INVENTION

1. Field of the Invention

The present invention relates to an apparatus for measuring both adhesion and friction between polymer, for example, PDMS polymer, and any other material that comes into contact with the polymer, and more particularly, to an apparatus for measuring physical properties, such as adhesive force, adhesive energy, frictional force, coefficient of friction, of a polymer hemisphere relative to a contact plate provided in the apparatus.

2. Description of the Related Art

Owing to recent technological development in micro-scale processes and nano-structure production fields, the manufacture of micro-scale elements or nano-structures, for use in the application of micro-machines (MEMS) and nano-machines (NEMS), is increasing. In particular, as one technique of manufacturing the nano-structures, a nano-imprinting lithography technique, that imprints polymers with nano-scale patterns using stamps made of certain materials, is being actively studied. The nano-imprinting lithography technique, however, suffers from the problem that adhesion and friction between the polymers and the stamps cause damage to the nano-scale patterns during the imprinting process. Nowadays, attempts are being made to apply adhesive properties of the nano-scale polymer structures to various applications, and accordingly, the measurement of adhesion and friction between the polymers and any other materials is a very important matter in the actual application of the polymers.

Conventionally, in the measurement of adhesion between polymers and corresponding plate-shaped contact means, Johnson-Kendall-Roberts (JKR) adhesion testers and other models have been used to measure required test data, for example, a contact area and weight. In the measurement of friction between the polymers and the contact means, other exclusive friction testers have been used.

As will be easily understood, using separately both the adhesion and friction testers is inconvenient when it is required to measure both adhesive and frictional properties of the polymers. Furthermore, when performance conditions of both the adhesion and friction testers, such as displacement and load-resolution, conflict with one another, it may cause measurement errors.

SUMMARY OF THE INVENTION

Therefore, the present invention has been made in view of the above problems, and it is an object of the present invention to provide an apparatus capable of accurately measuring adhesive and frictional properties, such as for example adhesive force, adhesive energy, frictional force and coefficient of friction, of a polymer hemisphere relative to a contact plate provided in the apparatus.

In accordance with the present invention, the above and other objects can be accomplished by the provision of an apparatus for measuring adhesive and frictional properties of polymers comprising: a body having a movable table installed to move along an X-axis and Y-axis and a vertical column positioned at a rear side of the movable table; a sample mount provided on the movable table and having a mirror to reflect surface images of a horizontal contact plate; a head assembly located at a front side of the column and having a polymer hemisphere used to press a surface of the contact plate to implement an adhesive force test; a camera device located at a front side of the mirror to capture the surface images of the contact plate during the adhesive force test; and a control device for analyzing various data inputted thereto during the adhesive force test, the data including a load applied to the contact plate via the head assembly and a predetermined load applying time as well as photography data related to the surface images of the contact plate captured by the camera device when the load is applied to the contact plate by the predetermined time.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Now, preferred embodiments of the present invention will be described in detail with reference to the annexed drawings.

Figure 1:
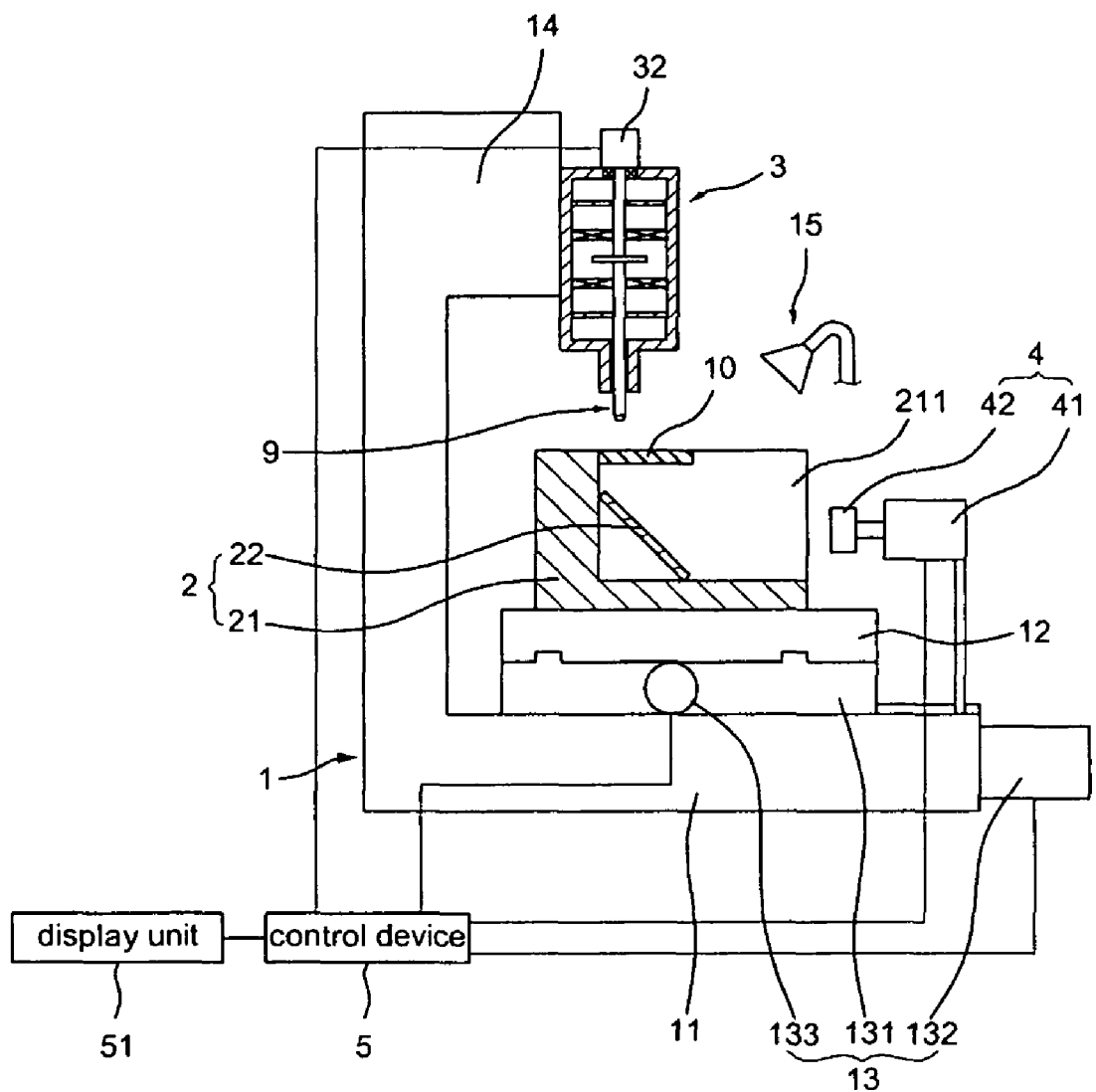
FIG. 1 is a diagram illustrating the overall configuration of a measuring apparatus according to the present invention.

FIG. 1 is a diagram illustrating the overall configuration of a measuring apparatus according to the present invention.

As shown in FIG. 1, the measuring apparatus of the present invention basically comprises a body 1, a head assembly 3, a sample mount 2, a camera device 4 and a control device 5. The body 1 includes a support frame 11, a movable table 12 disposed on the support frame 11 in an X-axis and Y-axis movable manner, and a vertical column 14 extending upward from a rear end of the support frame 11. The head assembly 3, located in front of an upper end of the column 14, has an actuator 32 that is electrically driven to vertically move a polymer hemisphere 9 fitted in the head assembly 3. The sample mount 2, provided on the movable table 12 of the body 1, centrally defines a recess 211, and a mirror 22 is obliquely installed in the recess 211. At the top of the sample mount 2 is provided a contact plate 10. The camera device 4 is located in front of the mirror 22 to capture images of a contact region between the polymer hemisphere 9 and the contact plate 10. The control device 5 serves to receive and analyze load and displacement signals measured by the head assembly 3 during a test.

The measuring apparatus of the present invention further comprises an illuminator 15 used to brightly illuminate the contact region between the polymer hemisphere 9 and the contact plate 10. Preferably, the illuminator 15 is positioned at a predetermined height aside the body 1.

Considering the camera device 4 in detail, it includes a CCD camera 41 and an optical microscope 42 located in front of a camera lens of the CCD camera 41. The use of the optical microscope 42 enables highly detailed photography of the contact region between the polymer hemisphere 9 and the contact plate 10.

In the case of a frictional force test using the measuring apparatus of the present invention configured as stated above, the movable table 12 is horizontally moved in a state wherein the polymer hemisphere 9 presses the contact plate 10. During the test, the camera device 4, including the CCD camera 41 and the optical microscope 42, is operated to capture images of the contact region between the hemisphere 9 and the contact plate 10, and the control device 5 analyzes various data inputted thereto, such as a load applied to the contact plate 10 via the head assembly 3 and a positioning system 13 and a predetermined load applying time as well as photography data related to surface images of the contact plate 10. Here, the surface images are captured by the CCD camera 41 while the load is applied to the contact plate 10 for the predetermined time.

The camera device 4, including the CCD camera 41 and the optical microscope 42, further includes an image sensor (not shown) that captures surface images of the contact plate 10, so as to permit the captured surface images of the contact plate 10 to be outputted to the control device 5.

The control device 5 includes a display unit 51 that displays the analyzed results in real time to permit an operator to visually confirm the results.

Figure 2:
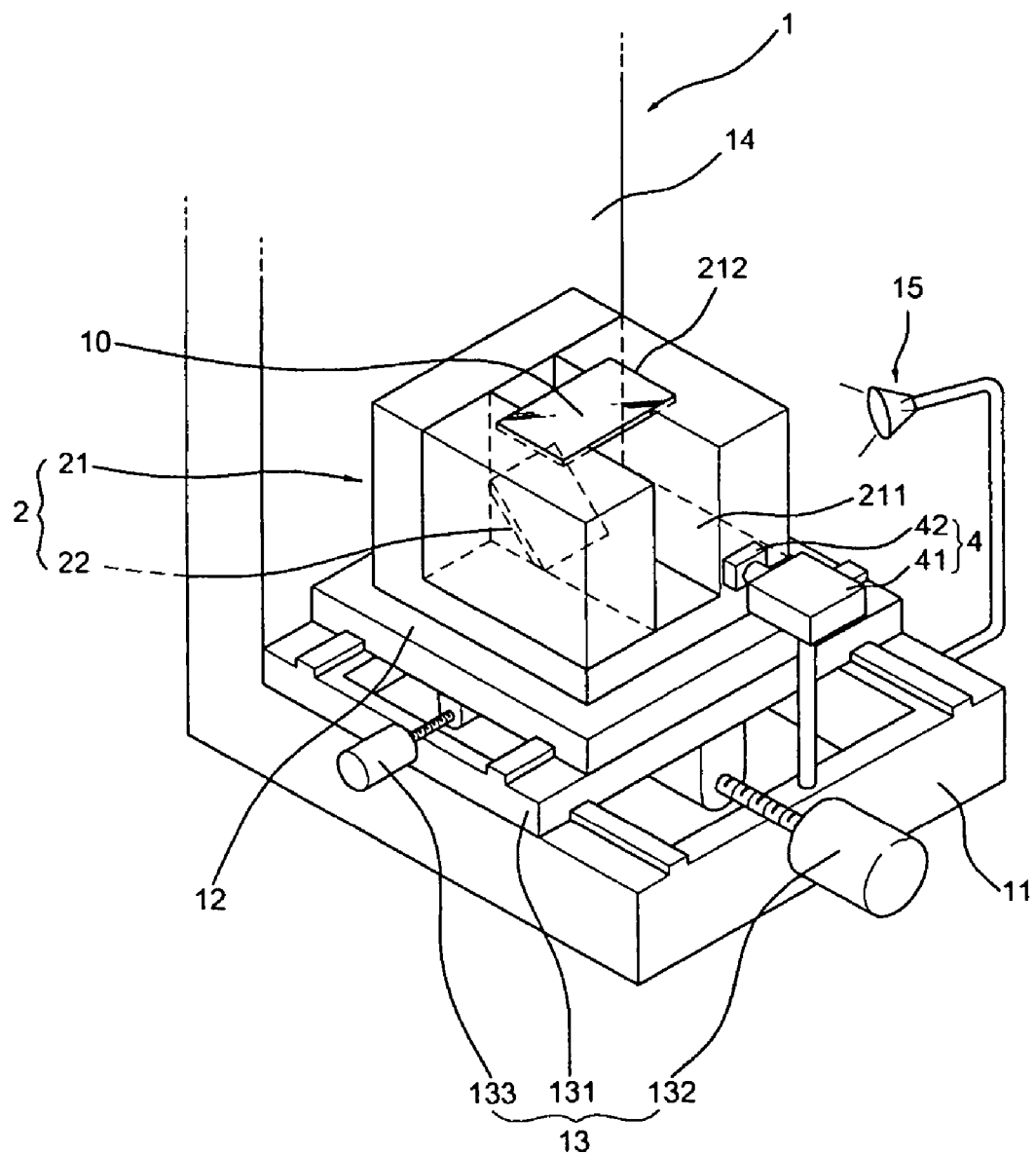
FIG. 2 is an enlarged perspective view of a sample mount provided in the measuring apparatus according to the present invention.

FIG. 2 is an enlarged perspective view of the sample mount 2 according to the present invention. Referring to FIG. 2, the positioning system 13, bearing the sample mount 2, serves to move the sample mount 2 along an X-axis and Y-axis for the initial setting of the sample mount 2, or to move the movable table 12 horizontally during the frictional force test.

For this, the positioning system 13 includes an X-axis moving plate 131 disposed on the support frame 11, an X-axis servo motor 132 having an X-axis guide and ball screw and adapted to move the X-axis moving plate 131 along the X-axis, and a Y-axis servo motor 133 having a Y-axis guide and ball screw and adapted to move the movable plate 12 along the Y-axis on the X-axis moving plate 131.

Although the X-axis and Y-axis servo motors 132 and 133 using the ball screws are shown in FIG. 2 and are explained as X-axis and Y-axis movement means, these servo motors 132 and 133 may be substituted by well known linear motors.

The adhesive force test and frictional force test according to the present invention are performed by making use of the contact plate 10 placed on the sample mount 2, which is, in turn, disposed on the movable table 12.

Such a sample mount 2 is comprised of a sample tray 21, bearing the contact plate 10 thereon, and the mirror 22 serving to reflect surface images of the contact plate 10 to thereby permit the camera device 4, including the CCD camera 41 and the optical microscope 42, to capture the surface images of the contact plate 10.

The sample tray 21 is affixed to the top of the movable plate 12, and the recess 211, which is opened at its front and upper sides, is centrally defined in the sample tray 21. The sample tray 21 further defines a recessed fitting portion 212 at an upper surface thereof so as to permit the contact plate 10 to be fixedly inserted thereinto.

The mirror 22 is obliquely installed in a region, where rear and bottom sides of the recess 211 meet, so as to reflect surface images of the contact plate 10 toward the camera device 4 including the CCD camera 41 and the optical microscope 42.

Figure 3:
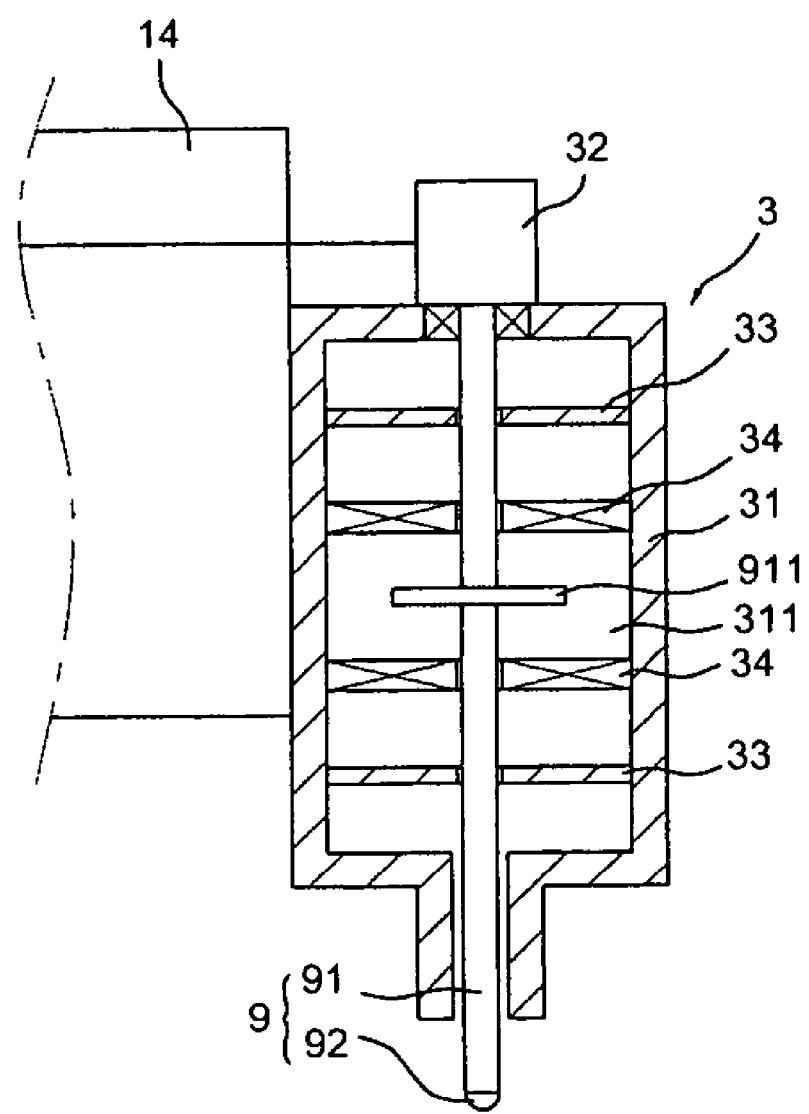
FIG. 3 is an enlarged sectional view of a head assembly provided in the measuring apparatus according to the present invention.

FIG. 3 is an enlarged sectional view of the head assembly 3 according to the present invention. As shown in FIG. 3, the head assembly 3 includes a case 31 affixed to the column 14 of the body 1 and having an interior space 311. The actuator 32 is disposed on the top of the case 31. The polymer hemisphere 9 of the head assembly 3 is connected to the bottom of the actuator 32 in a vertically movable manner, so that it protrudes downward from the case 31 under operation of one or more support springs 33 provided in the space 311. Inside the space 311 are further provided one or more displacement sensors that sense vertical positions of the polymer hemisphere 9.

The polymer hemisphere 9 consists of an indenter column 91 vertically movably penetrating the support springs 33 provided in the space 311, and an indenter tip 92 adhered to a lower end of the indenter column 91 by means of an adhesive.

The actuator 32 takes the form of a coil/magnet assembly, and serves to produce a magnetic field upon receiving electric power to thereby drive the polymer hemisphere 9 vertically.

The indenter column 91 is provided at a middle position thereof with a sensing plate 911 to permit the displacement sensors 34 to sense the position of the sensing plate 911. With such a configuration, when electric power is applied to the actuator 32 in the form of coil/magnet assembly, the polymer hemisphere 9 moves vertically, and simultaneously, the sensing plate 911, provided at the middle position of the indenter column 91, produces a magnetic field. Thereby, as the displacement sensors 34 measure the strength of the magnetic field produced by the sensing plate 911, the moved position of the polymer hemisphere 9 can be sensed. Here, the displacement sensors 34 are generally known magnetic-field measuring sensors.

The indenter tip 92 is formed by machining a plurality of hemispherical recesses at a panel surface, filling the recesses with polymers and separating the resulting polymer hemispheres from the recesses after solidification of the polymers.

Now, the operation of the present invention having a configuration as stated above will be explained.

As shown in FIGS. 1 to 3, the measuring apparatus of the present invention is an exclusive measuring apparatus for use in the measurement of both adhesive force and frictional force of the polymer hemisphere 9 relative to the contact plate 10 provided in the apparatus.

Hereinafter, procedures of both adhesive force test and frictional force test relative to the contact plate 10 will be explained successively.

First, upon an adhesive force test relative to the contact plate 10, as shown in FIGS. 1 to 3, the contact plate 10 is inserted into and fixed in the recessed fitting portion 212 of the sample mount 2 disposed on the movable plate 12.

Then, the positioning system 13 is operated to align the position of the contact plate 10 with the position of the polymer hemisphere 9 fitted in the head assembly 3. Thereby, the contact plate 10 is displaced to a test position where it will be pressed by the polymer hemisphere 9.

After aligning the positions of the contact plate 10 and the polymer hemisphere 9, the polymer hemisphere 9, supported by the support springs 33 inside the head assembly 3, is lowered and raised by predetermined distances for predetermined times. Such a vertical displacement of the polymer hemisphere 9 is performed as electric power is applied to the actuator 32 of the head assembly 3.

During the vertical displacement of the polymer hemisphere 9, the camera device 4, including the CCD camera 41 and the optical microscope 42, captures surface image of the contact plate 10 reflected by the mirror 22.

Finally, as the control device 5 analyzes various test data, including a load applied to the contact plate 10 via the head assembly 3, displacement and weight of the polymer hemisphere 9 and contact area between the polymer hemisphere 9 and the contact plate 10, deformation of the contact plate 10 due to the adhesive force of the polymer hemisphere 9 can be accurately measured.

Figure 4:
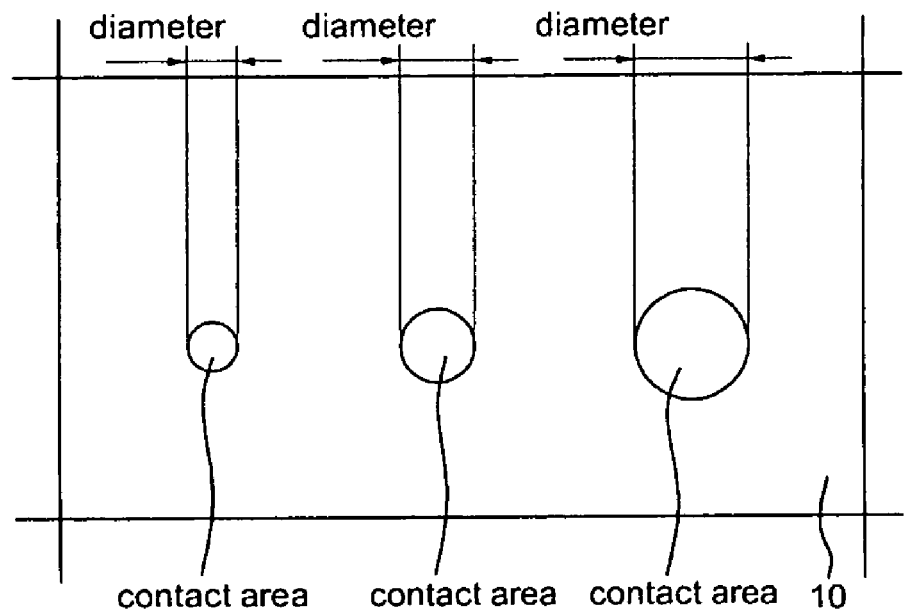
FIG. 4 is a schematic diagram illustrating different contact areas defined at a contact plate of the measuring apparatus as a result of an adhesive force test according to the present invention.

FIG. 4 is a schematic diagram illustrating different contact areas defined at the contact plate 10 during the adhesive force test according to the present invention. After completion of the adhesive force test, the resulting contact areas, defined at the contact plate 10 as the polymer hemisphere 9 presses the contact plate 10, have different diameters determined according to various test data, such as contact time, contact speed and contact force between the contact plate 10 and the polymer hemisphere 9.

Therefore, by making use of the contact areas and adhesive force measured according to the contact time, adhesive properties of the polymer hemisphere 9 relative to the contact plate 10 can be accurately measured.

Meanwhile, upon a frictional force test relative to the contact plate 10, as shown in FIGS. 1 to 3 and FIG. 5, the contact plate 10 is first inserted into and fixed in the recessed fitting portion 212 of the sample mount 2 disposed on the movable plate 12.

Then, the positioning system 13 is operated to align the position of the contact plate 10 with the position of the polymer hemisphere 9 fitted in the head assembly 3. Thereby, the contact plate 10 is displaced to the testing position where it will be pressed by the polymer hemisphere 9.

After aligning the positions of the contact plate 10 and the polymer hemisphere 9, the head assembly 3 is driven to apply a vertical load to the polymer hemisphere 9, so as to lower the polymer hemisphere 9 by a predetermined vertical displacement and to keep the lowered polymer hemisphere 9. The lowering of the polymer hemisphere 9 is performed as electric power is applied to the actuator 32 of the head assembly 3.

In succession, as the movable table 12 is moved horizontally via the positioning system 13, the surface of the contact plate 10, fixed to the sample mount 2, is scratched due to friction, thereby defining a contact area thereat. The frictional force caused by the horizontal movement of the movable table 12 is measured by the displacement sensors 34. After that, the polymer hemisphere 9 is raised again.

After completing raising of the polymer hemisphere 9, the camera device 4, including the CCD camera 41 and the optical microscope 42, captures surface images of the contact plate 10 reflected by the mirror 22.

Finally, as the control device 5 analyzes test data, including scratching speed, vertical load applied to the contact plate 10 via the head assembly 3, vertical displacement and vertical load of the polymer hemisphere 9, horizontal frictional force measured by the displacement sensors 34 as well as data related to the surface images of the contact plate 10 captured by the camera device 4 including the CCD camera 41 and the optical microscope 42, frictional properties of the polymer hemisphere 9 relative to contact plate 10 can be accurately measured.

Figure 5:
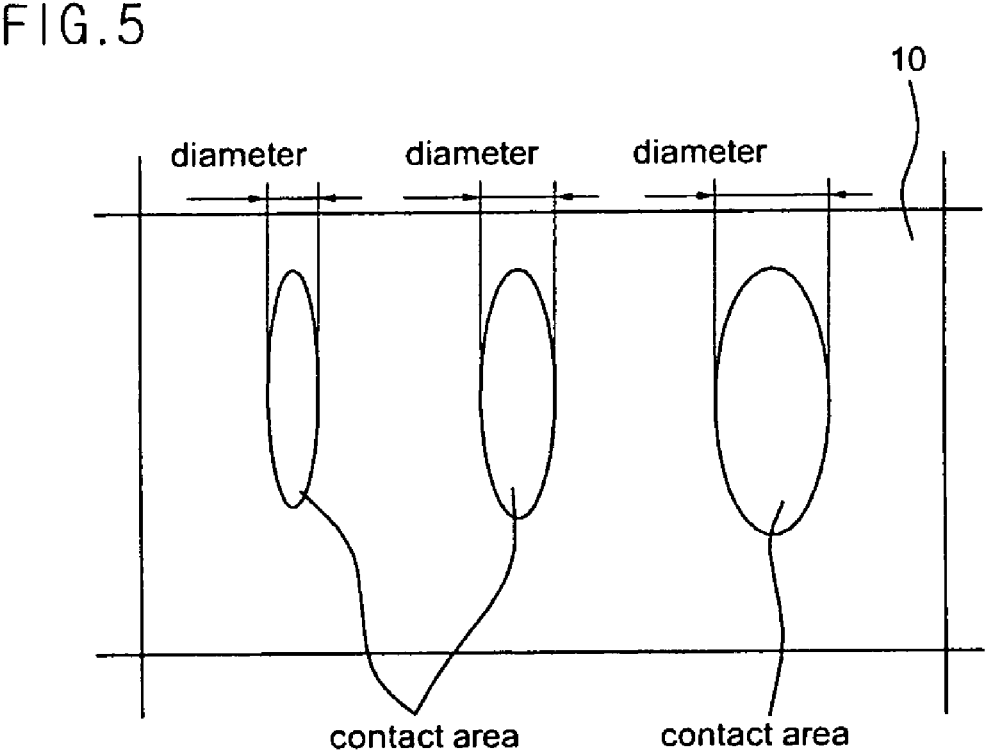
FIG. 5 is a schematic diagram illustrating different scratching contact areas defined at the contact plate as a result of a frictional force test according to the present invention.

FIG. 5 is a schematic diagram illustrating different contact areas defined at the contact plate 10 during the frictional force test according to the present invention. After completion of the frictional force test, the resulting contact areas, defined at the surface of the contact plate 10, have different diameters determined according to the various test data.

In this way, from the variation of the contact area according to the displacement, load and transfer speed during the frictional force test, frictional properties of the polymer hemisphere 9 relative to the contact plate 10 can be accurately measured.

As apparent from the above description, the present invention provides an apparatus capable of accurately measuring adhesive properties of polymers relative to a contact plate provided in the apparatus, thereby preventing possible damage to nano-scale patterns imprinted on certain products largely affected by the adhesive properties.

Further, the apparatus of the present invention can also accurately measure frictional properties of the polymers relative to the contact plate. This has the effect of widening the application range of polymers.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for measuring adhesive and frictional properties of polymers comprising:
    a body having a movable table installed to move via a positioning system along an X-axis and Y-axis and a vertical column positioned at a rear side of the movable table;
    a sample mount provided on the movable table and having a mirror to reflect surface images of a horizontal contact plate;
    a head assembly located at a front side of the column and having a polymer hemisphere used to press a surface of the contact plate to implement an adhesive force test;
    a camera device located at a front side of the mirror to capture the surface images of the contact plate during the adhesive force test; and
    a control device for analyzing various data inputted thereto during the adhesive force test, the data including a load applied to the contact plate via the head assembly and a predetermined load applying time as well as photography data related to the surface images of the contact plate captured by the camera device to determine the contact area between the polymer hemisphere and the contact plate when the load is applied to the contact plate by the predetermined time.

2. The apparatus as set forth in claim 1, wherein the movable table is moved horizontally in a state in which the polymer hemisphere presses the contact plate to implement a frictional force test,
    wherein, during the frictional force test, the camera device captures surface images of the contact plate, and the control device analyzes various data inputted thereto, including a load applied to the contact plate via the head assembly and the positioning system, displacement and transfer speed of the contact plate, and photography data related to the surface images of the contact plate captured by the camera device while the load is applied to the contact plate for the predetermined time.

3. The apparatus as set forth in claim 1, wherein the positioning system includes:
    an X-axis moving plate disposed on a support frame of the body;
    an X-axis servo motor having an X-axis guide and ball screw and adapted to move the X-axis moving plate along the X-axis; and
    a Y-axis servo motor having a Y-axis guide and ball screw and adapted to move the movable plate along the Y-axis on the X-axis moving plate.

4. The apparatus as set forth in claim 1, wherein the sample mount includes:
    a sample tray affixed to the top of the movable plate, the sample tray having a center recess opened at its front and upper sides and a recessed fitting portion defined above the recess to permit insertion and fixation of the contact plate therein; and the mirror obliquely installed in a region, where rear and bottom sides of the recess meet, and adapted to reflect the surface images of the contact plate to the camera device.

5. The apparatus as set forth in claim 1, wherein the head assembly includes:
   a case affixed to the column of the body and having an interior space;
   an actuator disposed on the top of the case;
   the polymer hemisphere connected to the bottom of the actuator in a vertically movable manner so that it protrudes downward from the case under operation of one or more support springs provided within the space; and
   one or more displacement sensors provided within the space and adapted to sense vertical positions of the polymer hemisphere.

6. The apparatus as set forth in claim 5, wherein the actuator takes the form of a coil/magnet assembly that produces a magnetic field upon receiving electric power to thereby move the polymer hemisphere vertically.

7. The apparatus as set forth in claim 6, wherein the polymer hemisphere includes:
   an indenter column vertically movably penetrating the support springs provided within the space; and
   an indenter tip adhered to a lower end of the indenter column by means of an adhesive.

8. The apparatus as set forth in claim 7, wherein the indenter column has a sensing plate provided at a middle position thereof, the sensing plate producing a magnetic field to permit the displacement sensors to sense a position thereof, and
   wherein the displacement sensors are sensors to measure a strength of the magnetic field produced by the sensing plate.

9. The apparatus as set forth in claim 7, wherein the indenter tip is formed by machining a plurality of hemispherical recesses at a panel surface, filling the recesses with polymers and separating the resulting polymer hemispheres from the recesses after solidification of the polymers.

10. The apparatus as set forth in claim 1, wherein the camera device includes:
    a CCD camera; and
    an optical microscope located at a front side of a camera lens of the CCD camera to enable highly detailed photography of a contact region between the polymer hemisphere and the contact plate.

11. The apparatus as set forth in claim 10, wherein the camera device further includes an image sensor to capture surface images of the contact plate.

12. The apparatus as set forth in claim 1, wherein the control device includes a display unit for displaying analyzed results in real time.

13. The apparatus as set forth in claim 1, further comprising:
    an illuminator to brightly illuminate a contact region between the polymer hemisphere and the contact plate.

14. The apparatus as set forth in claim 2, wherein the positioning system includes:
    an X-axis moving plate disposed on a support frame of the body;
    an X-axis servo motor having an X-axis guide and ball screw and adapted to move the X-axis moving plate along the X-axis; and
    a Y-axis servo motor having a Y-axis guide and ball screw and adapted to move the movable plate along the Y-axis on the X-axis moving plate.

15. The apparatus as set forth in claim 2, wherein the sample mount includes:
    a sample tray affixed to the top of the movable plate, the sample tray having a center recess opened at its front and upper sides and a recessed fitting portion defined above the recess to permit insertion and fixation of the contact plate therein; and
    the mirror obliquely installed in a region, where rear and bottom sides of the recess meet, and adapted to reflect the surface images of the contact plate to the camera device.

16. The apparatus as set forth in claim 2, wherein the head assembly includes:
    a case affixed to the column of the body and having an interior space;
    an actuator disposed on the top of the case;
    the polymer hemisphere connected to the bottom of the actuator in a vertically movable manner so that it protrudes downward from the case under operation of one or more support springs provided within the space; and
    one or more displacement sensors provided within the space and adapted to sense vertical positions of the polymer hemisphere.

17. The apparatus as set forth in claim 2, wherein the camera device includes:
    a CCD camera; and
    an optical microscope located at a front side of a camera lens of the CCD camera to enable highly detailed photography of a contact region between the polymer hemisphere and the contact plate.

18. The apparatus as set forth in claim 2, wherein the control device includes a display unit for displaying analyzed results in real time.

19. The apparatus as set forth in claim 2, further comprising:
    an illuminator to brightly illuminate a contact region between the polymer hemisphere and the contact plate.

* * * * *